(12) United States Patent
Rubino et al.

(10) Patent No.: US 9,107,804 B2
(45) Date of Patent: Aug. 18, 2015

(54) METHOD OF PREPARING BIOLOGICALLY ACTIVE FORMULATIONS

(75) Inventors: Orapin P. Rubino, Towaco, NJ (US); David M. Jones, Ramsey, NJ (US); Frank Bretschneider, Radeberg (DE); Karola Bretschneider, legal representative, Radeberg (DE); Peter Fankhauser, Ettingen (CH); Armin Prasch, Freiburg (DE)

(73) Assignee: Nortec Development Associates, Inc., Ramsey, NJ (US)

( * ) Notice: Subject to any disclaimer, the term of this patent is extended or adjusted under 35 U.S.C. 154(b) by 2398 days.

(21) Appl. No.: 10/728,196

(22) Filed: Dec. 4, 2003

(65) Prior Publication Data

US 2004/0185111 A1    Sep. 23, 2004

Related U.S. Application Data

(60) Provisional application No. 60/432,353, filed on Dec. 10, 2002.

(51) Int. Cl.
*A61K 9/16* (2006.01)
*A61J 3/02* (2006.01)

(52) U.S. Cl.
CPC .......... *A61J 3/02* (2013.01); *A61K 9/1605* (2013.01); *A61K 9/1635* (2013.01); *A61K 9/1652* (2013.01)

(58) Field of Classification Search
CPC ................. A61K 9/1605; A61J 3/02
See application file for complete search history.

(56) References Cited

U.S. PATENT DOCUMENTS

| | | | |
|---|---|---|---|
| 4,292,298 A | 9/1981 | Davis | |
| 4,588,366 A | 5/1986 | Glatt et al. | |
| 4,617,191 A | 10/1986 | Nowak | |
| RE32,307 E | 12/1986 | Glatt et al. | |
| 4,716,041 A * | 12/1987 | Kjornaes et al. | 424/468 |
| 4,783,337 A | 11/1988 | Wong et al. | |
| 4,820,521 A | 4/1989 | Panoz et al. | |
| 4,826,688 A | 5/1989 | Panoz et al. | |
| 4,832,967 A * | 5/1989 | Autant et al. | 426/96 |
| 4,891,230 A | 1/1990 | Geoghegan et al. | |
| 4,895,733 A | 1/1990 | Imanidis et al. | |
| 4,898,737 A | 2/1990 | Panoz et al. | |
| 4,900,557 A | 2/1990 | Dell et al. | |
| 4,963,365 A * | 10/1990 | Samejima et al. | 424/461 |
| 4,994,279 A | 2/1991 | Aoki et al. | |
| 5,011,640 A | 4/1991 | Zanchetta | |
| 5,049,394 A | 9/1991 | Howard et al. | |
| 5,082,668 A | 1/1992 | Wong et al. | |
| 5,084,287 A | 1/1992 | Ghebre-Sellassie et al. | |
| 5,132,142 A | 7/1992 | Jones et al. | |
| 5,229,135 A | 7/1993 | Philippon et al. | |
| 5,284,678 A | 2/1994 | Hirschfeld et al. | |
| 5,292,461 A | 3/1994 | Juch | |
| 5,445,829 A * | 8/1995 | Paradissis et al. | 424/480 |
| 5,458,888 A | 10/1995 | Chen | |
| 5,503,845 A | 4/1996 | Goede et al. | |
| 5,549,912 A | 8/1996 | Oshlack et al. | |
| 5,637,320 A | 6/1997 | Bourke et al. | |
| 5,709,885 A | 1/1998 | Hellen et al. | |
| 5,753,265 A | 5/1998 | Bergstrand et al. | |
| 5,783,215 A | 7/1998 | Arwidsson et al. | |
| 5,807,579 A | 9/1998 | Vilkov et al. | |
| 5,807,583 A | 9/1998 | Kristensen et al. | |
| 5,817,338 A | 10/1998 | Bergstrand et al. | |
| 5,891,474 A | 4/1999 | Busetti et al. | |
| 5,958,458 A | 9/1999 | Norling et al. | |
| 6,004,582 A * | 12/1999 | Faour et al. | 424/473 |
| 6,077,544 A | 6/2000 | Debregeas et al. | |
| 6,132,769 A | 10/2000 | Remon et al. | |
| 6,132,771 A | 10/2000 | Depui et al. | |

(Continued)

FOREIGN PATENT DOCUMENTS

| | | |
|---|---|---|
| EP | 0 378 404 A2 | 7/1990 |
| EP | 0 701 815 | 3/1996 |
| EP | EP 0 701 815 | 3/1996 |
| WO | WO 91/18590 | 12/1991 |
| WO | WO 93/07859 | 4/1993 |
| WO | WO 94/28882 | 12/1994 |
| WO | WO 95/34291 | 12/1995 |

(Continued)

OTHER PUBLICATIONS

Pollock et al., The Utility of Hydroxypropyl Methylcellulose as a Porosity Modifier in an Ethylcellulose Compression Coating, Dow Chemical, 2002, printed from http://msdssearch.dow.com/PublishedLiteratureDOWCOM/dh_0044/0901b80380044d9c.pdf?filepath=ethocel/pdfs/noreg/198-02076.pdf&fromPage=GetDoc, 4 pages.*

(Continued)

*Primary Examiner* — Gigi Huang
(74) *Attorney, Agent, or Firm* — Frommer Lawrence & Haug LLP

(57) ABSTRACT

The invention provides pellet for use as a core for a pharmaceutical dosage form having an inner and an outer zone where the inner zone includes a biologically active agent and said outer zone includes a layer formed by applying a substantially dry, free flowing inert powder which forms a non-tacky surface when placed in contact with water. The invention also provides a process for making pharmaceutical pellets where the core or at least one a layer on the core is formed by (a) contacting powder particles, adhering them to each other and compacting the adhered pellets by a rolling movement, wherein the degree of densification is controlled by the rolling movement; and (b) feeding a sufficient amount of a substantially dry, free flowing inert powder which forms a non-tacky surface when placed in contact with water to provide on said particles an outer zone including a layer formed from said substantially dry, free flowing inert powder.

14 Claims, 10 Drawing Sheets

(56) References Cited

U.S. PATENT DOCUMENTS

| | | | |
|---|---|---|---|
| 6,136,344 | A | 10/2000 | Depui et al. |
| 6,171,619 | B1 | 1/2001 | Fusejima et al. |
| 6,183,776 | B1 | 2/2001 | Depui et al. |
| 6,194,000 | B1 * | 2/2001 | Smith et al. .................. 424/458 |
| 6,197,347 | B1 | 3/2001 | Jan et al. |
| 6,224,909 | B1 | 5/2001 | Opitz et al. |
| 6,238,703 | B1 | 5/2001 | Jan et al. |
| 6,322,813 | B1 | 11/2001 | Green et al. |
| 6,354,728 | B1 | 3/2002 | Bretschneider et al. |
| 6,379,706 | B2 | 4/2002 | Opitz et al. |
| 6,387,404 | B2 | 5/2002 | Oshlack et al. |
| 6,449,689 | B1 | 9/2002 | Corcoran et al. |
| 6,449,869 | B1 | 9/2002 | Bretschneider et al. |
| 6,558,704 | B1 | 5/2003 | Bartholomaeus et al. |
| 6,586,010 | B1 | 7/2003 | Bertleff et al. |
| 6,962,717 | B1 * | 11/2005 | Huber et al. .................. 424/490 |

FOREIGN PATENT DOCUMENTS

| | | |
|---|---|---|
| WO | WO 00/16886 | 3/2000 |
| WO | WO 00/33819 | 6/2000 |
| WO | WO 0044353 A1 * | 8/2000 |
| ZA | 20000169 | 1/2000 |

OTHER PUBLICATIONS www.showmegold.org, Mesh to Micron Conversion Chart, http://www.showmegold.org/news/Mesh.htm, Jul. 28, 2014, 2 pages.*
International Search Report, Mar. 19, 2004.
International Search Report, Sep. 6, 2005.

* cited by examiner

METHOD OF PREPARING BIOLOGICALLY ACTIVE FORMULATIONS

The benefit of the filing date of Provisional Application Ser. No. 60/432,353, filed Dec. 10, 2002 is claimed.

BACKGROUND OF THE INVENTION

Oral solid dosage forms for biologically active agents have been prepared using various techniques that have been used to combine a powdered biologically active agent substance with a diluent and to form that mixture into a physical form that is suitable to make powder filled capsules, compressible particles for making tablets or coatable particles that are adapted for controlled release of active substances using matrix forming additives or membrane based controlled release coatings. As used herein, the term "biologically active agent" is used to include pharmaceutical compounds, pharmaceutical compositions, vitamins and nutrients.

The prior art has used various wet granulation, dry granulation, fluidized-bed, extrusion-spheronization and direct compression techniques to prepare particles in the form of granules or pellets for making solid dosage forms. In addition, spray-drying and spray congealing techniques have been used to form these types of particles.

The use of fluidized beds has been based on the use of top-spray or bottom-spray techniques using a Wurster air suspension column or a tangential-spray in rotary fluid-bed coater/granulator. Apparatus which have been used for coating and/or making pellets are described in U.S. Pat. No. 4,895,733; U.S. Pat. No. 5,132,142 and U.S. Pat. No. 6,354,728 all of which are incorporated by reference. South African patent 20000169 describes certain pharmaceutical pelleted formulations which contain up to 90 wt. % of a pharmaceutically active ingredient which are made by conventional spheronization techniques.

As used herein the term "pellet" means a substantially spherically shaped particle having a aspect ratio (a ratio of the length of the pellet divided by the width found at an angle of 90° in respect to the length) which is less than about 1.4, more preferably less than about 1.3, even more preferably less than about 1.2, especially preferably less than about 1.1, and most preferably less than about 1.05.

In one aspect, the present invention comprises the use of a rotating device that propels the powder particles onto a tangentially arranged surface which causes the powder particles to roll on said tangentially arranged surface. This process results in pellets having a controlled density, for instance highly dense pellets. These pellets may be formulated to have matrix controlled release properties or other types of release properties depending on the excipients which are employed. The pellets may be: adapted to contain high levels of biologically active agents, i.e. more than 90 wt %, such as more than 95 wt % and in particular more than 99 wt % and even more than 99.9 wt % of a biologically active agent in each pellet; pellets that are directly manufactured with a narrow size distribution without the need to carry out any substantial separation step and pellets that have multiple biologically active agent and/or rate release controlling coatings which will provide for controlled release of the active agents and/or physical separation of incompatible agents that are advantageously administered in combination. The pellet may comprise sustained release, pulsatile release, enteric release, immediate release or a combination of these release characteristics. In addition, the present invention provides novel processing methods which can optionally be used to reduce or eliminate the use of organic solvents, can produce smaller particles, can reduce the number of process steps and increase the total throughput per operating unit due to greatly reduced processing cycles.

SUMMARY OF THE INVENTION

The invention provides novel pellets adapted for biologically active preparations and a novel process for preparing said pellets. The pellets comprise a core and optionally one or more than one layer surrounding the core. The core and/or at least one layer is formed from powder particles.

The process of the invention comprises contacting of powder particles, adhering them to each other and compacting said adhered particles by a rolling movement.

The process of the invention comprises feeding powder particles into a device suitable for contacting and adhering said particles. According to one embodiment, the process may be started by feeding powder. In this case, pellet cores are formed from said powder particles. Powder particles are brought into contact such that some of the contacts lead to an adherence of particles to one another. It is usually preferred to use a pharmaceutically acceptable liquid in conjunction with the initial step of forming a pellet from a powder.

The particles may adhere to each other due to inherent properties of the material forming the particles. Powder particles will adhere to one another if they are sufficiently tacky. For some materials, this will depend on the temperature. Alternatively, the adherance of the powder particles may be enhanced by a pharmaceutically acceptable liquid, optionally comprising a binder.

In accordance with another embodiment, the process is carried out in the presence of preformed pellets, which are designated as cores. Such cores may be homogenous or may have an inner structure. Structured cores comprise cores made from different materials, arranged for instance in a layered form, as well as cores having zones of different densities. The cores may be prepared by the process of the invention. However, it is also possible to use cores formed by any other technique.

If the process of the invention is carried out in the presence of cores, the cores will be coated with a layer which is formed from powder particles. The cores are brought into contact with powder particles under such conditions that will cause the powder particles to adhere to the surface of the cores. Further powder particles are then contacted with powder particles which are already adhered to the surface of the cores to form what may be characterized as a further layer of powder particles, essentially as described above. In this way, a layer from powder particles surrounding the core is formed.

According to the invention, during both the formation of cores from powder particles and the coating of cores with a layer formed from powder particles, the particles are being formed into a compacted or densified layer which is usually more compact or dense than the starting product (i.e. has a higher bulk density).

The process of the present invention may be carried out in a rotating device that propels the powder particles onto a tangentially arranged surface which causes the powder particles to roll on said tangentially arranged surface and adhere to other particles thus forming pellets as the particles roll on the tangential surface. The rolling movement on the tangential surface is believed to result in a compacting force which is exerted on the adhering particles during the rolling movement.

The invention provides a process for making pellets adapted for biologically active preparations, comprising a core and optionally one or more layers surrounding said core, wherein said core and/or at least one of said layers is formed by contacting powder particles, adhering them to each other and compacting said adhered particles by a rolling movement, wherein the degree of densification is controlled by the energy uptake during the rolling movement.

In order to bring the pellets being formed into a rolling movement, kinetic energy has to be supplied to them. This can be achieved by moving, e.g. rotating, a moveable, e.g. rotatable, part of a suitable device with which the pellets being formed are in contact. Energy transfer between the moving part of the device and the pellets being formed will be based on frictional forces leading to a rolling movement of the pellets on surfaces of the device.

A preferred device comprises a rotor and a chamber wherein said rotor is located. On rotation of said rotor, the pellets being formed move in an outward direction on said rotor. Ultimately, the pellets come into contact with an inner wall of said chamber which is arranged to receive the outwardly moving pellets tangentially so that the pellets will begin to roll as they contact the inner wall of the chamber.

The preferred device also contains mechanical guide means arranged above said rotor such that the pellets being formed, after leaving said rotor, are guided back onto said rotor. Thus, the pellets being formed are put into circulation within the device. This allows the pellets being formed to repeatedly come into contact with powder particles fed and optionally with a pharmaceutically acceptable liquid. Thereby powder particles may adhere to the pellets being formed so that the pellets grow. The adhering powder particles are then subjected to a densification when the pellets undergo a rolling movement, e.g. on one of the surfaces of the device including the guide means. Because of the circulation of the pellets being formed in the device the densification process is continuously occurring as the powder is built up on the pellets.

An especially preferred device for carrying out the process of the invention is disclosed in U.S. Pat. No. 6,354,728. The use of this device offers the advantage of a particularly effective rolling movement of pellets in a concussion free manner. In this way, damaging the pellets being formed can be avoided. On the other hand, an effective uptake of energy can be achieved.

In addition to rolling on surfaces of the device in which the process is carried out, such as on the rotor surface, the inner wall of the chamber and the surface of the mechanical guide means, the rolling movement also involves rolling interactions within the bed of pellets being formed. These interactions are based on the spin of the pellets being formed. During the rolling movement of the pellets being formed on surfaces of the device used for carrying out the process, the pellets acquire a spin. A pellet being formed which rolls on surfaces of the device will transfer part of its spin to pellets in direct contact with it. Thus, even pellets which are, during a particular phase of the process, not in direct contact with a surface of the device, will perform a rolling movement, more precisely a rolling movement relative to other pellets, contributing to the densification of the powder particles.

Thus, it is preferable to carry out the process in such a manner that at least during a part of the processing time an individual pellet being formed comes into intimate contact with other pellets being formed. This requires the quantity of pellets processed in one batch to be sized to provide a sufficient number of intimate contacts with other pellets in order to cause the final pellets to have the desired properties. Generally, the apparatus that is used in the practice of the invention should be operated with an initial load of 25 to 100% of the volume capacity of the rotor. In any event, the apparatus should be operated with a sufficient load of pellets that individual pellets are continuously contacted with other pellets.

The interactions of the pellets with surfaces of the device and with each other, as the pellets are formed, results in the application of a high shearing 0 force on the pellets. It is believed that in this way, agglomeration of pellets with formation of unwanted lumps is avoided and the pellets formed have a spherical shape and a narrow particle size distribution.

Furthermore, it has now surprisingly been found that the degree of densification of the powder particles fed can be controlled by the energy uptake during the rolling movement. A larger energy uptake leads to a higher degree of densification.

The energy uptake can be measured as the proportion of the energy supplied to the device in which the process is carried out that is used to supply energy to the pellets being formed. This proportion of the energy corresponds to the energy supplied which is not consumed by the device itself. The energy uptake may be determined by monitoring the consumption of energy that is required to operate the apparatus. For example, the total electrical energy consumed less frictional losses due to the operation of the empty apparatus may be used to estimate the total energy uptake.

The energy supplied to the pellets being formed, for instance by rotating a rotor in a device containing the pellets, is taken up by the pellets as kinetic energy and as potential energy. This energy taken up is available for the rolling movement of the pellets. During the rolling movement, energy is used for densification of adhering powder particles.

If the rotation of a rotor is used to supply kinetic energy to the pellets being formed, the energy supply can be varied by varying the rotor speed. The rotor speed is a process parameter that can be varied to affect the velocity at which the pellets are moved during processing.

If other factors discussed below are kept constant, a higher rotor speed means a higher energy supply to the pellets being formed.

The density and the rate at which a biologically active agent is released from the pellets may be controlled by modifying the rotor speed which has a direct effect on the radial velocity at which the pellets move during processing. The rate of release may also be controlled by the use of other techniques as disclosed herein. The selected rotor speed will impart a radial velocity to the pellets which has been found to affect the density of the final pellet. Generally, it has been found that rotor speed that impart a radial velocity (measured at the tip of the rotor) of about 12-30 meters/second, will in the case of most biologically active materials, produce a pellet having a higher density and a slower release rate of the biologically active material as compared-to similar pellets made using a lower radial velocity. It has been observed that a rotor speed which induces a radial velocity of from 3-10 or more preferably from 4-7.5 meters/second will result in pellets which are less dense that the pellets which are produced using a higher radial velocity, i.e. 12-30 meters/second. The pellets containing a biologically active material which are made using a low radial velocity will generally show a release rate that is more rapid than pellets made with the same biologically active ingredient and the same excipients at the same radial velocity.

When biologically active materials are made into pellets according to the invention by using a high radial velocity, the release rates are retarded to a greater extent as compared to the release rates of pellets, made from the same materials, which are made in the same apparatus using conditions which impart a low radial velocity to the pellets. This effect is very pronounced when water insoluble biologically active materials are utilized in the manufacture of pellets.

As disclosed herein, the invention contemplates feeding, a portion of the powder used to make the pellet, in the form of a dry powder as the final or terminal step in the formation of the pellets. A terminal step of feeding the dry powder may be used to further modify the release properties of the biologically active material from pellets prepared according to the invention. As detailed in the examples prepared below, the pellets produced using a lower radial velocity will have a slower release rate, of the biologically active material, (from 20 to 40% slower at one in the case of ibuprofen) as compared to pellets made without the use of dry powder in the terminal step. The use of a dry powder feed in a terminal step for pellet formation where the pellets are produced using a high radial velocity is minimal (5-10% slower at one hour in the case of chlorpheniramine.

Release rates may be determined in a USP 23, Type II dissolution apparatus using water as a dissolution media. at 37° C. at a stirring speed of 100 rpm.

In general, it is believed that pellets made of water insoluble drugs will exhibit the greatest degree of release rate reduction when made using high radial velocities in the process of the invention.

The energy uptake does not only depend on the radial velocity of the pellets which is induced by a particular rotor speed, but also on other factors. One such factor is the construction or geometry of the device used to carry out the process. If a device such as disclosed in U.S. Pat. No. 6,354,728 is used, the energy uptake can be influenced by the number of guide vanes contained in the device.

The energy uptake will also depend on the load of the device, i.e. on the total amount of material contained in the device. The larger the weight of the material contained in the device, the larger are the compressive forces exerted on individual pellets due to the weight.

At a constant rotor speed in the same apparatus, the energy uptake will be higher for a higher load. This has to be taken into consideration for the control of the degree of densification since the load of the device will usually vary during the process of the invention. Making pellets will require feeding of material, such as powder particles and optionally a pharmaceutically acceptable liquid, so that the load will increase. If at least during a part of the processing time, a gas is supplied to remove solvent, this will tend to decrease the load or reduce the increase if other materials are simultaneously fed to the apparatus.

The energy uptake can further be adjusted by feeding a gas, such as air under ambient conditions, through the bed of the pellets being formed. This will be of particular relevance if the process is carried out at a fairly high loading of the capacity of the apparatus.

An apparatus suitable for carrying out this embodiment of the process of the invention is disclosed in U.S. Pat. No. 6,354,728. This device comprises a rotor located in a chamber such that an annular gap exists between the rotor and the inner wall of said chamber. Alternatively or in addition, the rotor may contain openings in its surface allowing a gas to pass through.

The gas stream, through the openings in the rotor, may be directed such that forces acting on the pellets being formed are reduced or increased. For instance, a gas may be led through openings in the rotor from below to reduce interactions between pellets and the rotor surface as well as among the pellets. This will reduce the densification of adhering powder particles. The quantity and flow rate of the gas which is passed through the bed of the pellets should not result in a significant fluidization of the pellet bed.

The degree of densification of the powder particles will also be influenced by the composition of the pellets being formed. One aspect of the composition of the pellets being formed is their liquid content. A higher liquid content will generally lead to a higher plasticity allowing a more effective densification. However, it has to be noted that, by the process of the invention, the degree of densification can be varied for a given composition by regulating the energy uptake of the pellets being formed when these pellets are subjected to a rolling movement, as described above.

The degree of densification of the powder particles comprised in the pellets made by the process of the invention may be determined by the absolute porosity of the formed pellet or layer. A high porosity corresponds to a low degree of densification, and vice versa.

The porosity may be visualized by microscopic techniques, for instance by scanning electron microscopy. Alternatively, the porosity may be determined by mercury intrusion.

The degree of densification will also be reflected in the density of the pellets prepared. A higher degree of densification leads to a higher density. The achieved absolute porosity, i.e. the percentage of the total void space with respect to the bulk volume, may vary between 0.5 and 30%. Preferably, the absolute porosity has a value of from 1 to 20%, more preferably of from 1 to 10%, and especially from 2 to 10%.

In a preferred embodiment, the invention provides a spherically shaped pharmaceutical pellet, comprising a core and optionally at least one or more layers surrounding said core, wherein said core and/or at least one of said layers is formed from pellets of a powder adhering to each other, wherein the degree of densification of said particles has a pre-determined value. This profile is expressed in terms of the absolute porosity of the core and/or at least one of said layers formed from powder particles and has a value of 0.5 to 30%, preferably 1 to 20% and more preferably 2-10%.

Preferably, the pellets have at least one layer formed from particles of a powder adhering to each other and in certain embodiments may have two or more layers adhering to one another.

The pellets may be made in such a manner that the degree of densification is such that a gradient of the degree of densification in a radial direction is achieved or separate concentric zones having varying levels of densification may be formed on each pellet, either in the core or in one or more layers. The degree of densification may be controlled so that at least one layer has a density that is lower than the bulk density of the starting powder.

Generally the pellets according to the invention will have a diameter of from 0.01 to 5 mm, such as from 0.1 to 2.5 mm. The layer or layers will each have a layer thickness of from 0.005 to 2.5 mm, such as from 0.05 to 1.25 mm. The pellets prepared according to the invention have a narrow particle size distribution such that a maximum of 20% by weight of the pellets have a diameter deviating from the average diameter of all by more than 20%. Preferably, a maximum of 10% by weight of the pellets have a diameter deviating from the average diameter of all, by more than 20%. Further preferably, a maximum of 20% by weight of the pellets have a diameter deviating from the average diameter of all pellets by more than 10% by weight. An especially preferred pellet product has a particle size distribution such that a maximum of 10% by weight of the pellets have a diameter deviating from the average diameter of all pellets by more than 10% by weight. All pervents by weight are based on the total weight of the pellets.

If desired, the pellets may be made from a core which is not substantially spherical.

A further embodiment of the pellet of the invention may comprise a core for a pharmaceutical dosage form, said core having an inner and an outer zone, said inner zone comprising a biologically active agent and said outer zone comprising a layer which is formed by applying to said inner zone, a substantially dry, free flowing inert powder which forms a non-tacky surface when placed in contact with water. An example of a non-tacky surface is the surface of microcrystalline cellulose which is wetted with water. The free flowing powder is used to prevent the pellets from sticking to one another or to the apparatus.

The invention also provides a process for making pharmaceutical pellets having a core with an inner and an outer zone as described herein wherein the core or at least one of said layers is formed by (a) contacting powder particles, adhering them to each other and compacting said adhered pellets by a rolling movement, wherein the degree of densification is controlled by the rolling movement; and (b) feeding a sufficient amount of a substantially dry, free flowing inert powder which forms a non-tacky surface when placed in contact with water to provide on said particles an outer zone comprising a layer formed from said substantially dry, free flowing inert powder.

A preferred embodiment of the invention provides a process of preparing pellets by:

(a) forming a powder mixture which comprises a binder and a biologically active agent;

(b) feeding said powder mixture which is optionally pre-wetted with from 0-60 wt % of a pharmaceutically acceptable liquid diluent, based on the total weight of the powder mixture and the pharmaceutically acceptable diluent, to an operating apparatus which comprises a rotor chamber having an axially extending cylindrical wall, means for passing air through said chamber from the bottom, spray means for feeding a liquid into said chamber, a rotor which rotates on a vertical rotor axis, said rotor being mounted in said rotor chamber, said rotor having a central horizontal surface and, in at least the radial outer third of said rotor, the shape of a conical shell with an outward and upward inclination of between 10° and 80°, said conical shell having a circularly shaped upper edge which lies in a plane which is perpendicular to the rotor axis, feed ports for introducing said powdered excipient, a plurality of guide vanes having an outer end affixed statically to said cylindrical wall of said rotor chamber above a plane formed by the upper edge of said conical shell of said rotor and an inner end which extends into said rotor chamber and is affixed tangentially to said cylindrical wall of said rotor chamber and having, in cross-section to the rotor axis, essentially the shape of an arc of a circle or a spiral, such that said powdered product which is circulated by kinetic energy by said rotor under the influence of kinetic energy, moves from said rotor to an inside surface of said guide vanes before falling back onto said rotor;

(c) rotating said rotor, while feeding air and spraying a pharmaceutically acceptable liquid into said rotor chamber for a sufficient amount of time to form solid pellets having a desired diameter; and (d) feeding a sufficient amount of a substantially dry, free flowing inert powder which forms a non-tacky surface when placed in contact with water to provide on said pellets an outer zone comprising a layer formed from said substantially dry, free flowing inert powder.

Accordingly, it is a primary object of the present invention to provide novel pellets which are useful for the delivery of biologically active agents.

It is also an object of the invention to provide novel pellets which can contain more than 99 wt % of an active biological agent, such as a pharmaceutical.

It is also an object of the invention to provide particles or pellets which have matrix release characteristics.

These and other objects of the invention-will become apparent from the appended specification.

DETAILED DESCRIPTION OF THE INVENTION

Figure 1:
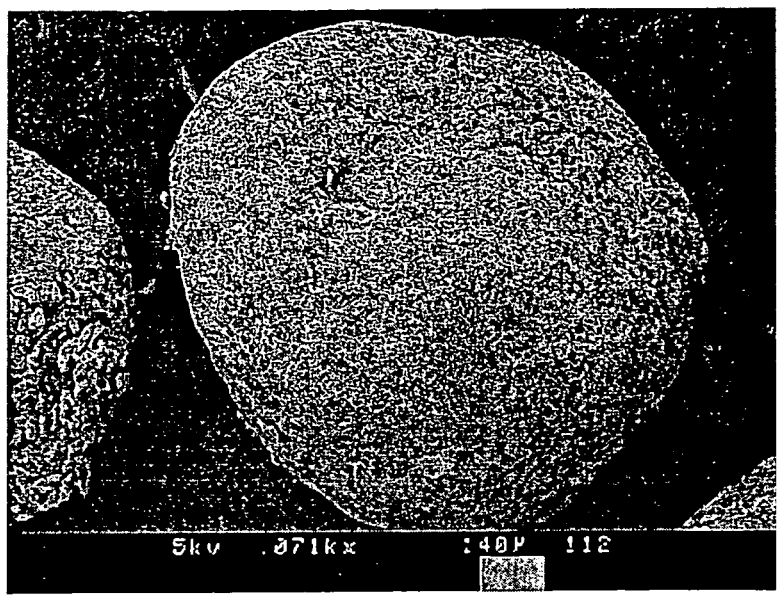
FIG. 1 is a scanning electron microscope (SEM) photograph which shows a cross-sectional view of a pellet of Example 1.

The pellets of the invention are typically prepared using an apparatus which propels particles against a tangentially arranged inner wall in such a manner that a rolling motion is imparted to the moving pellets. A liquid is fed into an apparatus such as the apparatus disclosed in U.S. Pat. No. 6,449,689 which is adapted to allow for the introduction of powder during the operation of the apparatus. In one embodiment of the invention, the process of the invention involves the introduction of a powder as a final step in the process in order to control and/or terminating pellet growth as well as assisting in the drying, rounding and smoothing of the pellets. The preferred apparatus is described in U.S. Pat. No. 6,449,869 and U.S. Pat. No. 6,354,728, both of which are incorporated by reference.

In one embodiment, the pellets of the invention, have an inner zone which has a structure that results from the application of a liquid to a powder in a particle stream under drying conditions. The liquid causes solid bridges to form and grow until a pellet having a desired size is obtained. At that point, the outer zone of the pellet is formed by feeding dry powder to the tumbling bed of pellets in order to cause the pellets to grow to their selected final dimension as well as to dry and smooth the pellets into a highly uniform and highly spherical product.

When the biologically active material is a pharmaceutical, it may be any physiologically or pharmacologically active substance that produces a local or systemic effect, in animals, including warm-blooded mammals, humans and primates The pharmaceutically acceptable liquid which is used in the formation of the pellets may comprise one or more components selected from the group consisting of biologically active ingredients, binders, diluents, disintegrants, lubricants, flavoring agents, coloring agents, surfactants, anti-sticking agents, osmotic agents, matrix forming polymers, film forming polymers, release controlling agents and mixtures thereof, in dissolved, suspended or dispersed form. Generally, only selected components will be employed to achieve the desired result for a given formulation. The particular formulation will determine if, when and how the listed components are added.

The process of the invention also includes the introduction, of a powder into a moving stream of partially formed pellets, as a means of controlling the growth of the pellets as well as assisting in the rounding and smoothing of the pellets.

The active pharmaceutical that can be delivered includes inorganic and organic compounds without limitation, including drugs that act on the peripheral nerves, adrenergic receptors, cholinergic receptors, nervous system, skeletal muscles, cardiovascular system, smooth muscles, blood circulatory system, synaptic sites, neuroeffector junctional sites, endocrine system, hormone systems, immunological system, reproductive system, skeletal system, autacoid systems, alimentary and excretory systems, inhibitory of autocoid systems, alimentary and excretory systems, inhibitory of autocoids and histamine systems. The active drug that can be delivered for acting on these recipients include anticonvulsants, analgesics, anti-inflammatories, calcium antagonists, anesthetics, antimicrobials, antimalarials, antiparasitic, antihypertensives, antihistamines, antipyretics, alpha-adrenergic agonist, alpha-blockers, biocides, bactericides, bronchial dilators, beta-adrenergic blocking drugs, contraceptives, cardiovascular drugs, calcium channel inhibitors, depressants, diagnostics, diuretics, electrolytes, hypnotics, hormonals, hyperglycemics, muscle contractants, muscle relaxants, ophthalmics, psychic energizers, parasympathomimetics, sedatives, sympathomimetics, tranquilizers, urinary tract drugs, vaginal drugs, vitamins, nonsteroidal anti-inflammatory drugs, angiotensin converting enzymes, polypeptide drugs, and the like.

Exemplary drugs that are very soluble in water and can be delivered by the pellets of this invention include prochlorperazine, ferrous sulfate, aminocaproic acid, potassium chloride, mecamylamine hydrochloride, procainamide hydrochloride, amphetamine sulfate, amphetamine hydrochloride, isoproteronol sulfate, methamphetamine hydrochloride, phenmetrazine hydrochloride, bethanechol chloride, methacholine chloride, pilocarpine hydrochloride, atropine sulfate, scopolamine bromide, isopropamide iodide, tridihexethyl chloride, phenformin hydrochloride, methylphenidate hydrochloride, cimetidine hydrochloride, theophylline cholinate, cephalexin hydrochloride, oxybutynin hydrochloride and the like.

Exemplary drugs that are poorly soluble in water and that can be delivered by the particles of this invention include diphenidol, meclizine hydrochloride, omeprazole prochlorperazine maleate, phenoxybenzamine, thiethylperzine maleate, anisindone, diphenadione, erythrityl tetranitrate, digoxin, isoflurophate, acetazolamide, methazolamide, bendro-flumethiazide, chlorpropamide, tolazamide, chlormadinone acetate, phenaglycodol, allopurinol, aluminum aspirin, methotrexate, acetyl sulfisoxazole, erythromycin, progestins, progestational, corticosteroids, hydrocortisone hydrocorticosterone acetate, cortisone acetate, triamcinolone, methyltestosterone, 17 beta-estradiol, ethinyl estradiol, ethinyl estradiol 3-methyl ether, prednisolone, 17 betahydroxyprogesterone acetate, 19 non-progesterone, norgesterel, norethindrone, norethisterone, norethiederone, progesterone, norgesterone, norethynodrel, and the like.

Examples of other drugs that can be formulated according to the present invention include aspirin, indomethacin, naproxen, fenoprofen, sulindac, indoprofen, nitroglycerin, isosorbide dinitrate, timolol, atenolol, alprenolol, cimetidine, clonidine, imipramine, levodopa, chloropromazine, methyldopa, dihydroxyphenylamine, pivaloyloxyethyl ester of alpha-methyldopa hydrochloride, theophylline, calcium gluconate, ketoprofen, ibuprofen, cephalexin, erythromycin, haloperidol, zomepirac, ferrous lactate, vincamine, diazepam, phenoxybenzamine, diltiazem, milrinone, captopril, madol, propranolol hydrochloride, quanbenz, hydrochlorothiazide, ranitidine, flurbiprofen, fenbufen, fluprofen, tolmetin, alolofenac, mefanamic, flufenamic, difuninal, nimodipine, nitrendipine, nisoldipine, nicardipine, felodipine, lidoflazine, tiapamil, gallopamil, amlodipine, mioflazine, lisinolpril, enalapril, captopril, ramipril, endlapriate, famotidine, nizatidine, sucralfate, etintidine, tertatolol, minoxidil, chlordiazepoxide, chlordiazepoxide hydrochloride, diazepam, amitriptylin hydrochloride, impramine hydrochloride, imipramine pamoate, enitabas, buproprion, and the like.

Other examples of biologically active materials include water soluble vitamins such as the B Vitamins, Vitamin C and the oil soluble vitamins such as Vitamin A, D, E and K. Neutraceuticals such as chondroitin, glucosamine, St. John's wort, saw palmetto and the like may also be formed into pellets according to the present invention.

In the case of pellets having an inner and an outer zone, the inner zone of the pellets may comprise, depending on the properties of the biological agent, from 0.1-99 wt % or from 3 to 90 wt % or from 5 to 60 wt % of a biologically active agent, based on the total weight of the pellet of one or more pharmaceutically acceptable binders and/or diluents based on the weight of the pellet. Suitable binders for use in the invention include those materials that impart cohesive properties to the powdered biologically active material when admixed dry or in the presence of a suitable solvent or liquid diluent. These materials commonly include starches such as pregelatinized starch, gelatin, and sugars such as sucrose, glucose, dextrose, molasses and lactose. Natural and synthetic gums include acacia, sodium alginate, extract of Irish moss, panwar gum, ghatti gum, mucilage of isapol husks, carboxymethyl cellulose, methylcellulose, microcrystalline cellulose, polyvinylpyrrolidone e.g. povidone U.S.P K30, Veegum, and larch arabogalactan. Binders are used in an effective amount, e.g. 1 to 10 wt %, based on the total weight of liquid and binder to cause a sufficient degree of agglomeration of the powders that stable particles are rapidly formed.

An outer zone may be formed by applying to the inner zone, a powder which comprises a substantially dry, free flowing inert powder which forms a non-tacky surface when placed in contact with water. Examples of such free flowing inert powders include water soluble and water insoluble materials. Examples of useful materials include microcrystalline cellulose, dicalcium phosphate, calcium sulfate, talc, an alkali metal stearate, silicon dioxide and calcium carbonate.

The powder which comprises a substantially dry, free flowing inert powder, may also include an active biological agent. For example, a particle having an outer zone formed from a substantially dry, free flowing inert powder and a biological agent, may contain, depending on the properties of the biological agent, from 0.1-99 wt % or from 3 to 90 wt % or from 5 to 60 wt % of a biologically active agent, based on the total weight of the pellet. In certain cases, it may be convenient to set aside from 5 to 35 wt %, preferably 10 to 25 wt % based on the weight of the total amount of the biological agent and the binder, prior to feeding the initial charge of binder and biological agent to the apparatus. The powder which is set aside may be used to form the outer zone of the pellets in the last stage of the process. This will result in the pellet having a homogeneous formulation but will still result in the formation of inner and outer zones having different densities.

Other additives that may be used in the pellet of the invention include diluents, lubricants, disintegrants, coloring agents and/or flavoring agents. The pellets may have a homogeneous or a heterogeneous core. The homogenous core may be made from one or more biologically active agents which may be homogeneously blended or may be applied as discrete layers. Heterogeneous cores will comprise a base which may be an inorganic or organic substrate to which concentric layers are applied using the process of the invention as described herein. The substrate may comprise an inorganic salt such as calcium phosphate or a non-pareil sugar-starch sphere or a microcrystalline cellulose seed.

In the case of a homogeneous or a heterogeneous core, a plurality of layers of biologically active materials, inert materials, or release controlling layers may be applied depending on the desired biological effect.

The pellets according to the invention may be made by using an apparatus that is described in U.S. Pat. No. 6,354,728. That apparatus comprises a rotor chamber having an axially extending cylindrical wall, means for passing air through said chamber from the bottom, spray means for feeding a liquid into said chamber, a rotor which rotates on a vertical rotor axis, said rotor being mounted in said rotor chamber, said rotor having a central horizontal surface and, in at least the radial outer third of said rotor, the shape of a conical shell with an outward and upward inclination of between 10° and 80°, said conical shell having a circularly shaped upper edge which lies in a plane which is perpendicular to the rotor axis, feed ports for introducing said powdered excipient, a plurality of guide vanes having an outer end affixed statically to said cylindrical wall of said rotor chamber above a plane formed by the upper edge of said conical shell of said rotor and an inner end which extends into said rotor chamber and is affixed tangentially to said cylindrical wall of said rotor chamber and having, in cross-section to the rotor axis, essentially the shape of an arc of a circle or a spiral, such that said powdered product which is circulated by kinetic energy by said rotor under the influence of kinetic energy, moves from said rotor to an inside surface of said guide vanes before it falls back onto said rotor.

When the desired pellet size is substantially achieved, it is preferred to feed dry powder to the apparatus and the apparatus is allowed to run for a period of 3 to 15 minutes, and preferably 5 to 10 minutes to complete the formation of the pellets.

It is also contemplated that some additional drying at a temperature of from about 30 to 100° C., and preferably from about 40 to 90° C. until the moisture content is from 1 to 10 wt %, based on the total weight of the pellets depending on the particular biologically active material and/or the particular excipients. Drying may be carried out in the preferred apparatus of the invention for making the pellets or in a separate dryer such as a fluid bed dryer.

The process is preferably based on the use of a minimal amount of liquid in order to avoid causing substantial swelling or gelation of any matrix forming materials which are placed on the pellet according to the invention.

The matrix forming material may be any swellable or non-swellable material that provides in vitro dissolution rates of a biologically active agent within the narrow ranges required to provide the desired plasma level of the biologically active agent over a desired interval which is typically 12 to 24 hours. Most matrix forming material will also provide for the release of the biologically active agent in a pH independent manner. Preferably the matrix is a controlled release matrix, although normal release matrices having a coating that controls the release of the drug may be used. Suitable water-swellable materials for inclusion in a controlled release matrix are (a) Hydrophilic polymers, such as gums, cellulose ethers, acrylic resins and protein derived materials. Of these polymers, the cellulose ethers, especially hydroxyalkylcelluloses and carboxyalkylcelluloses, are preferred. The pellets may contain between 1% and 35 wt % of a hydrophilic or hydrophobic polymer.

(b) Digestible, long chain ($C_8$-$C_{50}$, especially $C_{12}$-$C_{40}$), substituted or unsubstituted hydrocarbons, such as fatty acids, fatty alcohols, glyceryl esters of fatty acids, mineral and vegetable oils and waxes. Hydrocarbons having a melting point of between 25° and 90° C. are preferred. Of these long chain hydrocarbon materials, fatty (aliphatic) alcohols are preferred. The pellets may contain up to 60% (by weight) of at least one digestible, long chain hydrocarbon.

c) Polyalkylene glycols. The pellets may contain up to 60% (by weight) of at least one polyalkylene glycol.

One particular suitable matrix forming material comprises a water soluble hydroxyalkyl cellulose, at least one $C_{12}$-$C_{36}$, preferably $C_{14}$-$C_{22}$, aliphatic alcohol and, optionally, at least one polyalkylene glycol.

The hydroxyalkyl cellulose is preferably a hydroxy ($C_1$ to $C_6$) alkyl cellulose, such as hydroxypropylcellulose (HPC) or hydroxypropyl methylcellulose (HPMC). The nominal viscosity of the HPC or HPMC may be between 2,500 and 100,000 (2% w/v sol. at 20° C.) and preferably 5,000 to 50,000. The amount of the matrix forming material in the pellet will be determined, inter alia, by the precise rate of release required. This may be done by using conventional release rate testing procedures such as those described in U.S.P. 23, which testing procedures are incorporated by reference. When the pellets are formulated to contain a matrix polymer, the pellets will contain between 1% and 40 wt. %, especially between 5% and 20 wt. % of HPC or HPMC, based on the total weight of the pellets.

When forming pellets with water-swellable matrix forming materials, care should be exercised to prevent the matrix forming materials from swelling due to prolonged contact with liquid diluents in order to prevent the water-swellable matrix forming material from forming a gel during the pellet formation step.

Non-swellable matrix forming materials comprise water insoluble, dispersible polymers include the commercially available acrylic/methacrylic polymers as well as ethyl cellulose. The acrylic/methacrylic polymers are available under various tradenames such as Eudragit. These materials are used as non-swellable matrix forming polymers when they are admixed with biologically active compounds and various excipients which are formed into pellets according to the present invention. Generally from 1 to 30 wt %, of non-swellable matrix forming polymer, based on the weight of biologically active agent, excipient and non-swellable matrix forming polymer of may be admixed for the purpose of making a powder which may be formed into pellets according to the invention.

A release rate controlling polymer membrane may be applied to the pellets to provide for sustained release, delayed release, e.g. release in the small intestine by using a pH sensitive coating such as an enteric coating. Suitable enteric coatings include polymeric enteric coating material. The enteric coatings are "pH dependent" which describes the well known effect of an enteric coating which prevents release of the dosage form in the low pH conditions of the stomach but permits release in the higher pH conditions of the small intestine. The enteric coating will comprise from 1 to 25 wt % and preferably from 5 to 10 wt % of the total weight of the pellets. The enteric coating polymer may be selected from the group consisting of shellac, methacrylic acid copolymers, (Eudragit S or L) cellulose acetate phthalate, hydroxypropylmethylcellulose phthalate, hydroxypropylmethylcellulose acetate succinate, cellulose acetate trimellitate and polyvinyl acetate phthalate. Methacrylic acid copolymer, Type B USP/NFXXII which dissolves at a pH above about 6.0 is preferred. The thickness of the coating is selected to provide the desired release rate depending on the thickness of the coating and the particular coating.

A commercially available copolymer is Eudragit S100 which is based on methacrylic acid and methyl methacrylate and has a weight average molecular weight of about 150,000. Other auxiliary coating aids such as a minor amount (1-5 wt % based on the active core component and the total weight of the final coating) of a plasticizer such as acetyltributyl citrate, triacetin, acetylated monoglyceride, rape oil, olive oil, sesame oil, acetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof in combination with an antisticking agent which may be a silicate such as talc. An antisticking agent, such as talc may be added in an amount which is effective to prevent sticking of the pellets. These components may be added to the methacrylic acid copolymer in combination with appropriate solvents.

A sustained release coated pellet may be coated with a polymeric material which will substantially maintain its integrity in the varying pH conditions of the gastrointestinal tract but is permeable to the particular biologically active agent which is being formulated. The sustained release coating is used at a level that is selected to release the biologically active agent at a rate that will provide the desired in vivo release characteristics that will provide the desired plasma profile for the selected biologically active agent. Polymers such as ethyl cellulose, cellulose acetate, cellulose acetate butyrate, or an acrylic. copolymer which when used in a sufficient amount will cause the coated pellet to release the biologically active agent after ingestion of the dosage form of the invention. Materials such as Eudragit RS 30D; RS 100; NE 30D; RL 30D or RL 100 may be used to prepare the delayed pulse pellet. One such useful material is an acrylate copolymer which has a permeability which is independent of pH. That acrylate copolymer is commercially available as Eudragit RS30D which is available as a 30 wt % aqueous dispersion of copolymers of acrylic and methacrylic acid esters, having a number average molecular weight of 150,000 with a low content of quaternary ammonium groups. Other auxiliary coating aids such as a minor amount (3-7 wt % based on the total weight of the active core component and the total weight of the final coating) of a plasticizer such as acetyltributyl citrate, triacetin, acetylated monoglyceride, rape oil, olive oil, sesame oil, cetyltriethylcitrate, glycerin sorbitol, diethyloxalate, diethylmalate, diethylfumarate, dibutylsuccinate, diethylmalonate, dioctylphthalate, dibutylsebacate, triethylcitrate, tributylcitrate, glyceroltributyrate, polyethyleneglycol (molecular weight of from 380 to 420), propylene glycol and mixtures thereof.

If a disintegrant is employed, it may comprise from 2 to 8 wt. % based on the total weight of the pellet, of starch, clay, celluloses, algins, gums and cross-linked polymers. Super disintegrants such as cross-linked cellulose, cross-linked polyvinylpyrrolidone, Croscarmellose sodium, carboxymethylcellulose and the like may also be employed if it desired to have a rapid release of the biologically active agent.

Conventional osmotic agents include non-toxic inorganic salts such as sodium chloride, potassium chloride, disodium phosphate and the like or water soluble non-toxic organic compounds such as lactose, sucrose, dextrose and the like. Antisticking agents such as talc may be employed to achieve any required result.

The pellets of the invention may be placed in hard or soft gelatin capsules to prepare finished dosage forms suitable for administration to a patient or they may be used to prepare compressed tablets using suitable cushioning agents, diluents, binders, disintegrants and lubricants.

DESCRIPTION OF THE PREFERRED EMBODIMENTS

Example 1

Chlorpheniramine maleate pellets (10% concentration), were produced at low rotor speed (300 rpm) which induces a radial velocity of about 4.7 meters/second in the pellets as compared to pellets produced at high rotor speed (1000 rpm) which induces a radial velocity of about meters/second in an apparatus described in U.S. Pat. No. 6,354,728.

Process conditions: Low rotor speed:

| Formulation: | |
|---|---|
| Chlorpheniramine maleate (CPM) | 100 g |
| Microcrystalline cellulose (grade 101) | 900 g |

1. Blend CPM and MCC in a plastic bag.
2. Prewet CPM/MCC blend with 300 g water in a VG (vertical high shear granulator).
3. Transfer prewetted blend into an apparatus made according to U.S. Pat. No. 6,354,728.
4. Set the apparatus controls as follow:
Spray rate 35 g/min
   Four baffles (shallow)
   Atomization air pressure 30%
   Rotor speed (low) 300 rpm
5. Spray—700-1000 g of water
6. Finish spraying water.
7. Discharge the wet pellets. Dry in a GPCG-1 (granulator dryer) at a temperature of 80° C. to a moisture content of <3%
FIG. 1 is an SEM of a cross-sectional view of the pellet produced in Example 1.
Analytical Testing:
Dissolution of chlorpheniramine maleate from pellets (841-1190 micron), using USP dissolution testing at 60 min time point 98.2%
Bulk density of pellets (841-1190 micron) 0.67 g/cc

Example 2

| Formulation: | |
|---|---|
| Chlorpheniramine maleate (CPM) | 100 g |
| MCC (grade 101) | 900 g |

1. Blend CPM and MCC in a plastic bag.
2. Prewet CPM/MCC blend with 300 g water in a VG.
3. Transfer prewetted blend into the apparatus used in Example 1.
4. Set the parameter for the apparatus as follow: spray rate 35 g/min.

| Four baffles (shallow) | |
|---|---|
| Atomization air pressure | 30% |
| Rotor speed (high) | 1000 rpm |

5. Spray~700-1000 g of water.
6. Finish spraying water.
7. Discharge the wet pellets. Dry in a CPCG-1 at a temperature of 80° C. to a moisture content of <3%.

Figure 2:
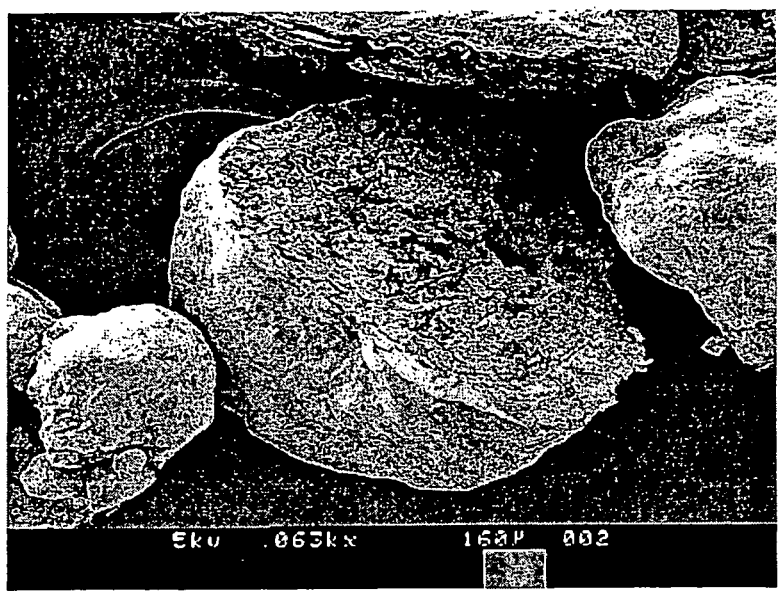
FIG. 2 is a scanning electron microscope (SEM) photograph which shows a cross-sectional view of a pellet of Example 2.

FIG. 2 is an SEM which shows a cross-sectional view of the pellet produced in Example 2.

Analytical Testing:
Dissolution of chlorpheniramine maleate from pellets (841-1190 micron), using USP dissolution testing at 60 min time point 89.5%
Bulk density of pellets (841-1190 micron) 0.80 g/cc
Pellets produced using low rotor speed (Example 1) and high rotor speed (Example 2) have different physical characteristics (pellet shape, bulk density, pellet structure).
The pellets produced using high rotor speed at the stated conditions are irregular in shape (not spherical). These pellets may be used as an intermediate in the preparation of spherical pellets.
Drug release of pellets produced using low rotor speed and high rotor speed also differ. Chlorpheniramine maleate pellets that were produced using low rotor speed (Example 1) have lower bulk density (0.67 vs. 0.80 g/cc) and higher drug release at 60 min time point (98.2 vs. 89.5%) when compared to the pellets produced using high rotor speed (Example 2).

Example 3

| Formulation: | |
|---|---|
| Chlorpheniramine maleate (CPM) | 100 g |
| MCC (grade 101) | 900 g |

1. Blend CPM and MCC in a plastic bag.
2. Prewet CPM/MCC blend with 300 g water in a VG.
3. Transfer prewetted blend into the apparatus of Example 1.
4. Set the parameter for processing as follows: Spray rate 35 g/min

| Four baffles (shallow) | |
|---|---|
| Atomization air pressure | 30% |
| Rotor speed (low) | 300 rpm |

5. After 600 g water sprayed, change the rotor speed to 1000 rpm, continue spraying water. Additional amount of water to spray~200-400 g.
6. Finish spraying water.
7. Discharge the wet pellets. Dry in a GPCG-1 to moisture of <3%

Figure 3:
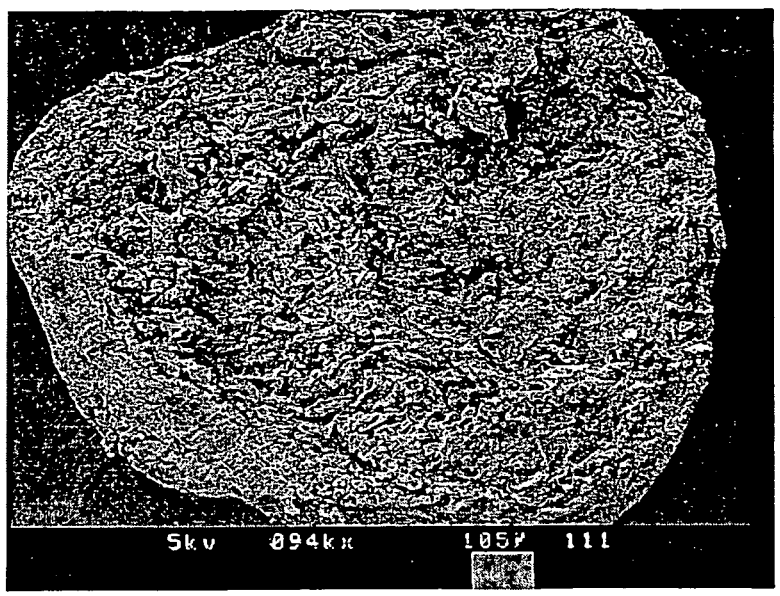
FIG. 3 is a scanning electron microscope (SEM) photograph which shows a cross-sectional view of a pellet of Example 3.

FIG. 3 is an SEM which shows a cross-sectional view of the pellet produced in Example 3.

Analytical Testing:
Dissolution of chlorpheniramine maleate from pellets (841-1190 micron), using USP dissolution testing at 60 min time point 90.4%
Bulk density of pellets (841-1190 micron) 0.79 g/cc Summary:
The pellets produced using low speed initially and adjusting to high rotor speed during processing (Example 3) have higher bulk density (0.79 vs. 0.67 g/cc) and lower drug release (90.4 vs. 98.2%) when compared to pellets produced using low rotor speed (Example 1). Surface morphology of the pellets produced using low speed initially and adjusting to high rotor speed during processing (Example 3) was also smoother than the surface the pellets produced using low rotor speed (Example 1).

Summary: Effect of Rotor Speed

TABLE 1

Effect of Rotor Speed on Bulk Density and Drug Release of Chlorpheniramine maleate Pellets (10% concentration)

| Rotor speed | Low (Ex 1) | High (Ex 2) | Low/High (Ex 3) |
|---|---|---|---|
| Bulk dens. | 0.67 g/cc | 0.80 g/cc | 0.79 g/cc |
| Drug rel. (60 min timepoint) | 98.2% | 89.5% | 90.4% |

Example 4

To demonstrate the effect of the powder feeding step, 20% of total weight of blend was set aside to powder feed at the end of spraying process, process is described below. The pellets are compared to the pellets produced at the same low or high rotor speed, described in Example 1 and Example 2.

| Formulation: | |
|---|---|
| Chlorpheniramine maleate (CPM) | 100 g |
| MCC (grade 101) | 900 g |

1. Blend CPM and MCC in a plastic bag. Weigh 200 g for powder feeding.
2. Prewet CPM/MCC blend with 250 g water in a VG.

3. Transfer prewetted blend into the apparatus of Example 1.
4. Set the parameter for processing as follows: Spray rate 35 g/min
   Four baffles (shallow)
   Atomization air pressure 30%
   Rotor speed (low) 300 rpm
5. Spray~700-1000 g of water
6. Start powder feed at powder feed rate of 40 g/min. Reduce spray rate to 20 g/min and continue spraying water.
7. Finish spraying water, finish powder feed.
8. Discharge the wet pellets. Dry in a CPCG-1 to moisture of <3%

Figure 4:
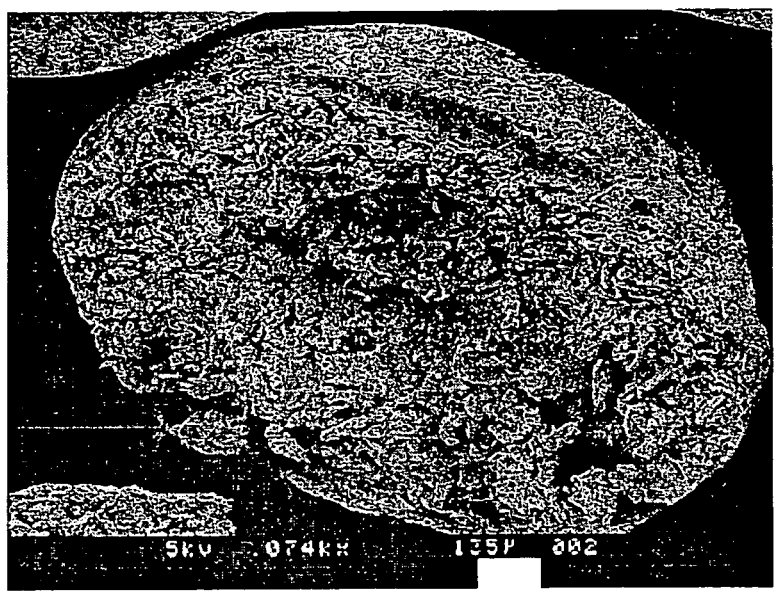
FIG. 4 is a scanning electron microscope (SEM) photograph which shows a cross-sectional view of a pellet of Example 4.

FIG. 4 is an SEM photograph which shows a cross-sectional view of a pellet made by the procedure of Example 4.

Analytical Testing:
Dissolution of chlorpheniramine maleate from pellets (841-1190 micron), using USP dissolution testing at 60 min time point 101.9%
Bulk density of pellets (841-1190 micron) 0.76 g/cc Example 5

High rotor speed with powder feeding step

| Formulation: | |
| --- | --- |
| Chlorpheniramine maleate (CPM) | 100 g |
| MCC (grade 101) | 900 g |

1. Blend CPM and MCC in a plastic bag. Weigh 200 g for powder feeding.
2. Prewet CPM/MCC blend with 250 g water in a VG.
3. Transfer prewetted blend into the apparatus of Example 1.
4. Set the parameter for processing as follows: Spray rate 35 g/min.

| Four baffles (shallow) | |
| --- | --- |
| Atomization air pressure | 30% |
| Rotor speed (high) | 1000 rpm |

5. Spray~700-1000 g of water.
6. Start powder feed at powder feed rate of ~40 g/min. Reduce spray rate to 20 g/min and continue spraying water.
7. Finish spraying water, finish powder feed.
8. Discharge the wet pellets. Dry in a CPCG-1 to moisture of <3%.

Figure 5:
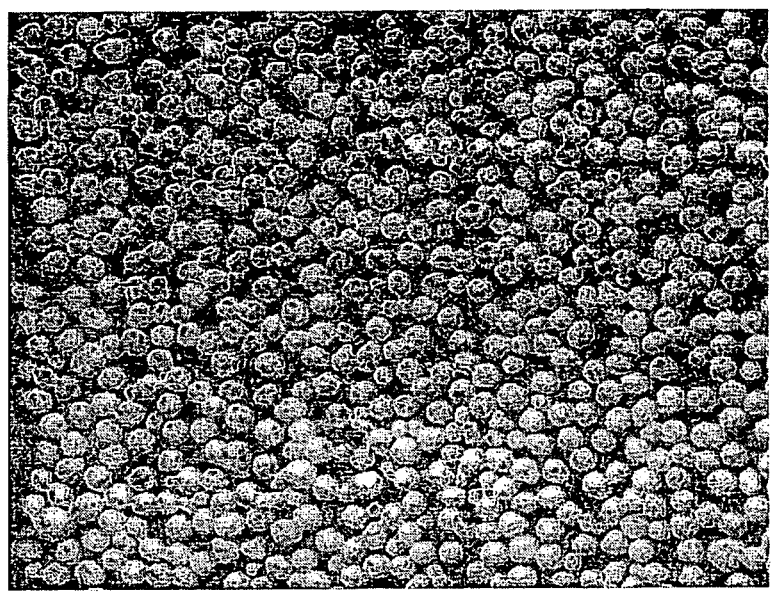
FIG. 5 is a photograph of a magnified view of the gross morphology of the pellets of Example 5.

FIG. 5 shows the gross morphology of pellets made by the procedure of Example 5.

Analytical testing;
Dissolution of chlorpheniramine maleate from pellets (841-1190 micron), using USP 23 dissolution apparatus with water at 60 minute time point 84.7%
Bulk density of pellets (841-1190 micron) 0.79 g/cc Summary:
The processes without powder feeding step (Example 1 for low rotor speed and Example 2 for high rotor speed) were compared to the processes with powder feeding step (Example 4 for low rotor speed and Example 5 for high rotor speed). Other process parameters were kept constant so that the only variable during the two processes is powder feeding step.

Powder feeding step at the end of spraying process improved pellets shape and surface morphology of pellets for both low and high rotor speed condition (comparing Example 4 to Example 1 and Example 5 to Example 2). The effect of powder feeding on pellet shape was more pronounced at high rotor speed condition (significantly more spherical with powder feeding step—Example 4 compared to Example 2). The surface morphology was smoother for the pellet produced using powder feeding step (Example 4 compared to Example 1.).

Chlorpheniramine release from the pellets was not significantly affected by powder feeding step at low rotor speed condition (98.2% without powder feeding step vs. 101.9% with powder feeding step). At high rotor speed condition, pellets produced using powder feeding step has slightly lower drug release at 60 min time point (84.7% vs. 89.5% without powder feeding step).

Example 6

1.8 kg. of pellets (av. diameter 710-850 microns) that were made from microcrystalline cellulose (101) were placed in an apparatus according to U.S. Pat. No. 6,354,728. The rotary atomizer was used to spray into the apparatus a solution of chlorpheniramine maleate (CPM) (0.2 kg dissolved in 0.2 kg. of water at a rate of about 19 g/min. which was increased to a rate of about 30 g/min. The radial velocity was 8.9 meters/second. After the CPM solution spraying is complete, the process was continued in the same apparatus by introducing a water spray at about 30 g/min. and a powder blend of 0.8 kg of carboxypolymethylene (Carbopol 971P) and 0.2 kg of talc (S500) at a rate of approximately 30-50 g/min. The water spray rate is increased to about 38 g/min. The pellets begin to stick to one another and the powder feed and water spray are stopped and about 230 g of microcrystalline cellulose powder (MCC) is added to the apparatus. Spraying is restarted at a rate of about 38 g/min. and the powder blend is fed intermittently with additional 230 g portions of MCC. The water spray rate is decreased to about 9 g/min. and all, of the powder blend is fed to the apparatus.

An additional 270 g portion of MCC is fed with a water spray at a rate of about 37 g/min. and the powder is fed at a rate of about 30-50 g/min. After the powder feed is complete, the process is terminated and the pellets are dried in a GPCG-1 fluid bed drier at about 80° C. until the pellets are dried to about a 5 wt % average moisture content based on the total weight of the pellets.

The average diameter of the pellets was approximately 800 microns.

The pellets were tested to determine the rate at which the CPM was released in a USP 23 Type II apparatus at 37° C. at a paddle speed of 100 rpm in water. The results were as follows:

| Time | % CPM released |
| --- | --- |
| 0.5 h | 26.3 |
| 1 hr | 29.8 |
| 2 hr | 34.0 |
| 3 hr | 44.2 |
| 6 hr | 55.0 |
| 8 hr | 59.9 |
| 12 hr | 61.1 |

Figure 6:
FIG. 6 is a scanning electron microscope (SEM) photograph which shows a cross-sectional view of a pellet of Example 6.

FIG. 6 is an SEM photograph which shows a cross-section of a pellet made by the procedure of Example 6.

Example 7

Pellets were made according to the following procedure:

| | |
|---|---|
| Ibuprofen 25 (BASF) | 3,600 g |
| Polyvinylpyrrolidone (PVP K-30)) | 200 g |
| MCC (Vivapor 101) | 200 g |

The blend was mixed in a VG for 1.5 min. A 1.5 kg portion was segregated for later use as a powder feed during the last step of the process. Then 2.5 kg of the blended powders were then loaded into an apparatus that is described in U.S. Pat. No. 6,354,728.

Figure 7:
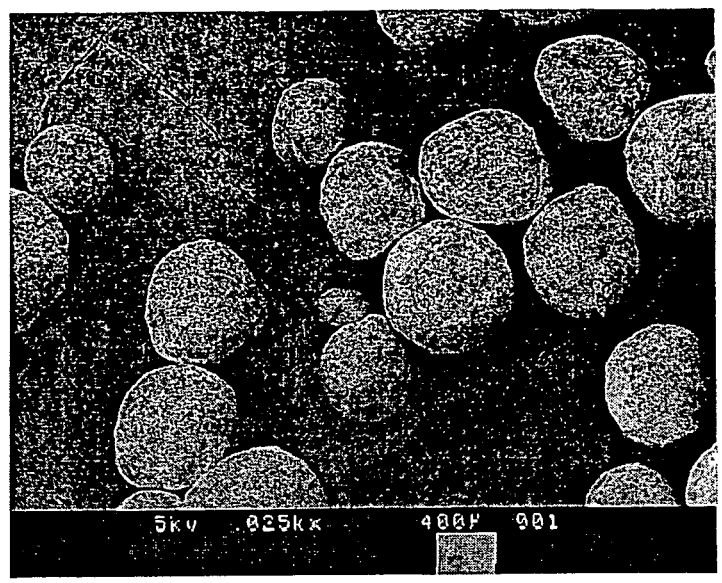
FIG. 7 is a photograph of a magnified view of the gross morphology of the pellets of Example 7.

Spraying was initiated with water containing 0.1w % of Tween 80. The spray rate was 19 g/min. and the initial rotor speed was 475 rpm (8.9 meters/sec.) (70%) gradually increasing to 550 rpm (10.4 meters/sec. (80%). After 320 g was sprayed, the spray rate was increased to about 40 g/min. which seemed to be too fast. The spray rate was then reduced to about 29 g/min. When 750 g had been sprayed, it appeared that some powder had been sucked in through the powder feed port. After 863 g had been sprayed, the spray rate was increased to about 40 g/min. and powder feeding was started at a rate of about 66 g/min. The liquid spray rate was decreased to about 29 g/min. Spraying was stopped after 1379 g had been sprayed and all of the powder (1.25 kg) was added and the rotor was operated for about 4 minutes after the powder feeding was complete. The total process time was about 50 min. The pellets were dried in a GPCG-1 at 55-65° C. until the product temperature was 45° C. The gross morphology of the pellets is shown in FIG. 7. The average size is approximately 800 microns.

Example 8

Ibuprofen pellets (10% concentration) that are produced at low rotor speed (300 rpm) are compared to pellets produced at high rotor speed (1000 rpm).

II

| | |
|---|---|
| Ibuprofen (IBU) | 100 g |
| MCC (grade101) | 900 g |

1. Blend IBU and MCC in a plastic bag.
2. Prewet IBU/MCC blend with 300 g water in a VG.
3. Transfer prewetted blend into the apparatus of Example 1.
4. Set the parameter for processing as follows: Spray rate 35 g/min
   i. Four baffles (shallow)
   ii. Atomization air pressure 30%
   iii. Rotor speed (low) 300 rpm
5. Spray~700-1000 g of water
6. Finish spraying water.
7. Discharge the wet pellets. Dry in a GPCG-1 to moisture of <5%

Analytical Testing:
Dissolution of Ibuprofen from pellets (841-1190 micron), using USP dissolution testing at 60 min time point 72.1%
Bulk density of pellets (841-1190 micron) 0.66 g/cc
Process conditions: High rotor speed

| Formulation: | |
|---|---|
| Ibuprofen (IBU) | 100 g |
| MCC (grade101) | 900 g |

1. Blend IBU and MCC in a plastic bag.
2. Prewet IBU/MCC blend with 300 g water in a VG.
3. Transfer prewetted blend into the apparatus of Example 1. Set the parameter for processing as follows: Spray rate 35 g/min.
   Four baffles (shallow)
   Atomization air pressure 30%
   Rotor speed (high) 1000 rpm
4. Spray~700-1000 g of water.
5. Finish spraying water.
6. Discharge the wet pellets. Dry in a GPCG-1 to moisture of <5%.

Figure 8A:
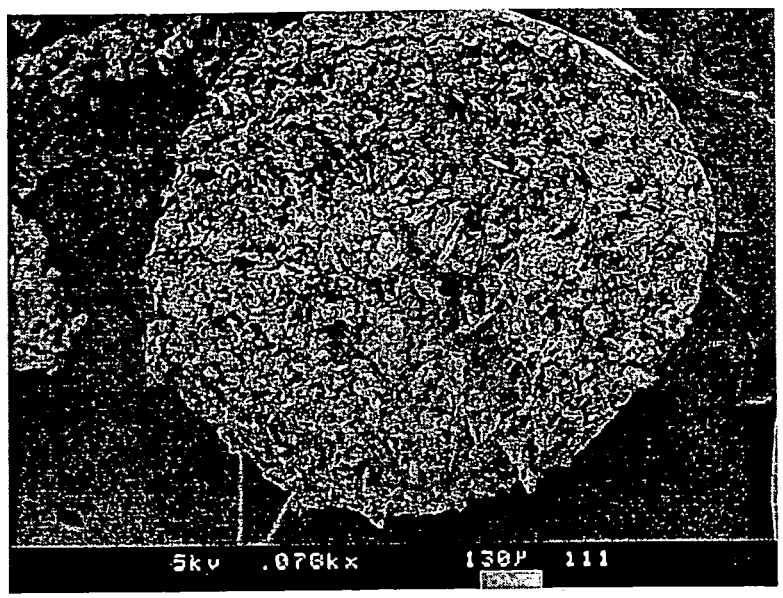
FIG. 8A is a scanning electron microscope (SEM) photograph of a cross-sectional view of a pellet of Example 8 made using a low rotor speed.
Figure 8B:
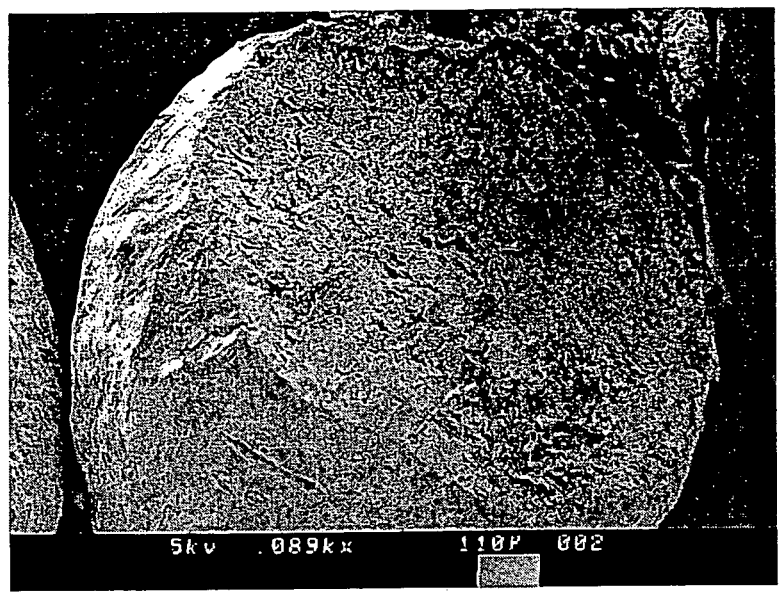
FIG. 8B is a scanning electron microscope (SEM) photograph of a cross-sectional view of a pellet of Example 8 made using a high rotor speed.

Analytical Testing:
Dissolution of Ibuprofen from pellets (841-1190 micron), using USP dissolution testing at 60 min time point 38.6%
Bulk density of pellets (841-1190 micron) 0.80 g/cc
FIG. 8A is a SEM of a cross-section of a pellet made using a low rotor speed and FIG. 8B is a SEM of a cross-section of a pellet made at high rotor speed.

Summary:
Ibuprofen pellets produced using low rotor speed and high rotor speed have different physical characteristics (particle shape, bulk density, pellet structure). The pellets produced using high rotor speed are not as spherical as the pellets produced using low rotor speed.

Drug release of pellets produced using low rotor speed and high rotor speed also differs. Ibuprofen, which is a water insoluble compound, released at significantly slower rate from pellets produced at high rotor speed than from pellets produced at low rotor speed (38.6% vs. 72.1%). The bulk density of pellets produced at high rotor speed was higher than that of pellets produced at low rotor speed (0.80 vs. 0.66 g/cc). Pellet structure (under scanning electron microscope) was denser for pellets produced at high rotor speed.

Example 9

Pellets were made using a combination of low and high rotor speeds as follows:

| Formulation: | |
|---|---|
| Ibuprofen (IBU) | 100 g |
| MCC (grade101) | 900 g |

1. Blend IBU and MCC in a plastic bag.
2. Prewet IBU/MCC blend with 300 g water in a VG.
3. Transfer prewetted blend into the apparatus of Example 1.

4. Set the parameter for the apparatus of Example 1 processing as follows:
5. Spray rate 35 g/min
  Four baffles (shallow)
  Atomization air pressure 30%
  Rotor speed (low) 300 rpm
6. After 600 g water sprayed, change the rotor speed to 1000 rpm, continue spraying water. Additional amount of water to spray~200-400 g.
7. Finish spraying water.
8. Discharge the wet pellets. Dry in a GPCG-1 to moisture of <5%

Figure 9:
FIG. 9 is a scanning electron microscope (SEM) photograph which shows a cross-sectional view of a pellet of Example 9.

Analytical Testing:
Dissolution of Ibuprofen from pellets (841-1190 micron), using USP dissolution testing at 60 min time point 60.2%%
Bulk density of pellets (841-1190 micron) 0.75 g/cc
FIG. 9 is an SEM of a cross-section of a pellet made according to Example 9.
Summary:
The Ibuprofen pellets produced using low speed initially and adjusting to high rotor speed during processing (Example 9) have higher bulk density (0.75 vs. 0.66 g/cc) and lower drug release (60.2% vs. 72.1%) when compared to pellets produced using low rotor speed (Example 8). Surface morphology of the pellets produced using low speed initially and adjusting to high rotor speed during processing was slightly smoother than the surface the pellets produced using low rotor speed Summary: Effect of Rotor Speed
Table II.1: Effect of Rotor Speed on Bulk Density and Drug Release of Ibuprofen Pellets (10% concentration)

|  | Rotor Speed | | |
| --- | --- | --- | --- |
|  | Low rotor speed (Ex. 8) | High Rotor Speed (Ex. 8) | Low rotor speed initially, adjusted to high rotor speed during processing (Ex. 9) |
| Bulk density | 0.66 g/cc | 0.80 g/cc | 0.75 g/cc |
| Drug release (60 min timepoint) | 72.1% | 38.6% | 60.2% |

Example 10

To investigate the effect of powder feeding step, 20% of total weight of blend was set aside to powder feed at the end of spraying process, process is described below. The pellets are compared to the pellets produced at the same low or high rotor speed, described in Example 8.

Formulation:

| Ibuprofen (IBU) | 100 g |
| --- | --- |
| MCC (grade101) | 900 g |

1. Blend IBU and MCC in a plastic bag. Weigh 200 g for powder feeding.
2. Prewet IBU/MCC blend with 250 g water in a VG.
3. Transfer prewetted blend into apparatus of Example 1.
4. Set the parameter for processing as follows: Spray rate 35 g/min
  Four baffles (shallow)
  Atomization air pressure 30%
  Rotor speed (low) 300 rpm
5. Spray~700-1000 g of water
6. Start powder feed at powder feed rate of 40. g/min. Reduce spray rate to 20 g/min and continue spraying water.
7. Finish spraying water, finish powder feed.
8. Discharge the wet pellets. Dry in a GPCG-1 to moisture of <5%

Analytical Testing:
Dissolution of Ibuprofen from pellets (841-1190 micron), using USP dissolution testing at 60 min time point 47.3%
Bulk density of pellets (841-1190 micron) 0.70 g/cc
Process conditions: High rotor speed

| Ibuprofen (IBU) | 100 g |
| --- | --- |
| MCC (grade101) | 900 g |

1. Blend IBU and MCC in a plastic bag. Weigh 200 g for powder feeding.
2. Prewet IBU/MCC blend with 250 g water in a VG.
3. Transfer prewetted blend into the apparatus of Example 1.
4. Set the parameter for the apparatus of Example 1 as follow:
5. Spray rate 35 g/min.
  Four baffles (shallow)
  Atomization air pressure 30%
  Rotor speed (high) 1000 rpm
6. Spray~700-1000 g of water.
7. Start powder feed at powder feed rate of ~40 g/min. Reduce spray rate to 20 g/min and continue spraying water.
8. Finish spraying water, finish powder feed.
9. Discharge the wet pellets. Dry in a GPCG-1 to moisture of <5%

Analytical Testing:
Dissolution of Ibuprofen from pellets (841-1190 micron), using USP dissolution testing at 60 min time point 44.9%
Bulk density of pellets (841-1190 micron) 0.77 g/cc
Summary:
The processes without powder feeding step for low rotor speed and for high rotor speed (Example 8) were compared to the processes with powder feeding step for low rotor speed and for high rotor speed (Example 10). Other process parameters were kept constant so that the only variable during the two processes is powder feeding step.
For Ibuprofen, which is a water insoluble compound, effect of powder feeding step on pellet shape and morphology was not as pronounced as in the case of Chlorpheniramine maleate which is a water soluble compound.
The effect of powder feeding step on the Ibuprofen release rate was very significant. This effect is more distinct for Ibuprofen (water insoluble compound) than Chlorpheniramine maleate (water soluble compound). At low rotor speed condition, the powder feeding step led to a significant decrease in Ibuprofen release from pellets (at 60 min timepoint, 47.3% vs. 72.1% without powder feeding step). The bulk density of pellets produced using powder feeding step was slightly higher (0.70 g/cc vs. 0.66 g/cc without feeding step).
At high rotor speed condition, the powder feeding step led to slight increase in Ibuprofen release (at 60 min timepoint, 44.9% vs. 38.6% without powder feeding step). The bulk density of pellets produced using powder feeding step was slightly lower (0.77 g/cc vs. 0.88 g/cc without powder feeding step).

Dissolution Profiles of Ibuprofen Pellets (prepared at low rotor speed, high rotor speed and low rotor speed with powder feeding).

The Ibuprofen pellets prepared in Example 8 and Example were submitted for dissolution-testing for 24 hours.

The dissolution profiles are summarized in Table 2.

Dissolution or Ibuprofens from Pellets Prepared at different process conditions

| Time (hours) | Low Rotor Speed (Ex. 8) | High Rotor Speed (Ex. 8) | Low Rotor Speed with powder feed (Ex. 10) |
|---|---|---|---|
| 0.25 | 34.2 | 19.2 | 24.9 |
| 1 | 72.1 | 39.6 | 49.0 |
| 2 | 94.3 | 54.2 | 66.8 |
| 4 | 103.0 | 71.9 | 87.6 |
| 6 | 103.1 | 83.3 | 98.5 |
| 8 | 103.3 | 91.0 | 101.6 |
| 12 | 103.5 | 97.5 | 101.9 |
| 18 | 103.4 | 97.7 | 102.2 |
| 24 | 103.7 | 98.1 | 102.3 |
| Bulk Density (g/cc) | 0.66 | 0.80 | 0.70 |

Using Ibuprofen as an example of a water insoluble compound, it is possible to produce sustained release drug pellets by controlling the process conditions of the invention (low vs. high rotor speed) that affect density of pellets which in turn affect drug release from the pellets.

The process of the invention allows the process parameters to be adjusted during pellet formation. These adjustments can affect physical characteristics, as well as drug release, of pellets. It is possible to add additional powder (after core pellets are formed). This addition of powder can affect pellets shape, morphology and release of drug from the pellets. The powder feeding step for Ibuprofen pellets, which is a water insoluble compound, affected the release rate significantly, especially at low rotor speed conditions. It is possible to produce sustained release pellets by varying density of pellets being formed and by addition of powder during processing.

The invention claimed is:

1. A pellet which is adapted for use as a core for a pharmaceutical dosage form, said pellet comprising:
    an inner zone which is located in a center of the pellet, the inner zone being homogeneous and comprising a biologically active agent; and
    an outer zone comprising: a substantially dry, free-flowing inert powder;
    a swellable matrix forming polymer; and
    and a non-swellable matrix forming polymer;
    wherein the powder includes at least one component from the group consisting of microcrystalline cellulose, dicalcium phosphate, calcium sulfate, talc, an alkali metal stearate, silicon dioxide, and calcium carbonate;
    wherein the swellable matrix forming polymer includes at least one component selected from the group consisting of hydroxypropyl methyl cellulose, hydroxypropyl cellulose, hydroxyethyl cellulose, and carboxypolymethylene;
    wherein the non-swellable matrix forming polymer includes at least one component selected from the group consisting of acrylic/methacrylic polymers and ethyl cellulose;
    wherein the outer zone is formed on the inner zone without first drying the inner zone; and
    wherein the pellet has a cross section which is visually homogeneous such that there is no visible distinction between the inner zone and the outer zone when viewed by a scanning electron microscope.

2. The pellet as defined in claim 1;
wherein the inner zone comprises:
    0.1-95 wt % of one or more pharmaceutically acceptable components selected from the group consisting of binders and diluents; and
    99.9-5.0 wt % of the biologically active agent.

3. The pellet as defined in claim 1;
wherein said outer zone further comprises from 0.1-99 wt % of a biologically active agent.

4. The pellet as defined in claim 1;
wherein the at least one component of the powder includes microcrystalline cellulose.

5. The pellet as defined in claim 1;
wherein said inner zone additionally comprises one or more components selected from the group consisting of lubricants, disintegrants, flavors, surfactants, anti-sticking agents, osmotic agents, and mixtures thereof.

6. The pellet as defined n claim 1;
wherein said outer zone additionally comprises one or more components selected from the group consisting of binders, diluents, disintegrants, lubricants, flavors, surfactants, anti-sticking agents, osmotic agents, and mixtures thereof.

7. The pellet as defined in claim 1;
wherein said inner comprises a swellable matrix forming polymer.

8. The pellet as defined in claim 1;
wherein said inner comprises a non-swellable matrix forming polymer.

9. The pellet as defined in claim 1, further comprising:
one or more layers which comprise a release rate controlling polymer.

10. The pellet as defined in claim 9;
wherein the release rate controlling polymer comprises at least one component selected from the group consisting of ethyl cellulose, methacrylic acid copolymers, cellulose acetate phthalate, hydroxypropylmethylcellulose phthalate, hydroxypropylmethylcellulose acetate succinate, cellulose acetate trimellitate, and polyvinyl acetate phthalate.

11. A pharmaceutical dosage form which comprises:
coated pellets comprising:
    as a core a pellet as defined in claim 1; and
    one or more release rate controlling coatings selected from the group consisting of delayed release coatings, sustained release coatings, and mixtures thereof.

12. The pharmaceutical dosage form as defined in claim 11;
wherein the controlled release coating is a sustained release coating.

13. The pharmaceutical dosage form as defined in claim 11;
wherein the dosage form includes different populations of coated pellets having different controlled release coatings.

14. The pharmaceutical dosage form as defined in claim 11;
wherein the dosage form is a hard gelatin capsule.

* * * * *